United States Patent

Nishimura et al.

[11] 3,988,456
[45] Oct. 26, 1976

[54] 1,2-DIPHENYLETHANOLAMINE DERIVATIVES AND THEIR SALTS AND THE PREPARATION THEREOF

[75] Inventors: Haruki Nishimura, Ikeda; Hitoshi Uno, Takatsuki; Kagayaki Natsuka, Ibaraki; Noriaki Shimokawa, Nagaokakyo; Masanao Shimizu, Kobe; Hideo Nakamura, Tenri, all of Japan

[73] Assignee: Dainippon Pharmaceutical Co., Ltd., Osaka, Japan

[22] Filed: Mar. 24, 1975

[21] Appl. No.: 561,336

[30] Foreign Application Priority Data
Mar. 29, 1974 Japan............................ 49-36537

[52] U.S. Cl............... 424/250; 260/268 PH; 260/268 R; 260/268 H
[51] Int. Cl.²...................................... C07D 295/10
[58] Field of Search....... 260/268 R, 268 PH, 268 H; 424/250

[56] References Cited
OTHER PUBLICATIONS
Albro et al., Chemical Abstracts, vol. 44, pp. 7856–7857i, (1950).

*Primary Examiner*—Nicholas S. Rizzo
*Assistant Examiner*—Jose Tovar
*Attorney, Agent, or Firm*—Stevens, Davis, Miller & Mosher

[57] ABSTRACT

1,2-Diphenylethanolamine derivatives of the formula:

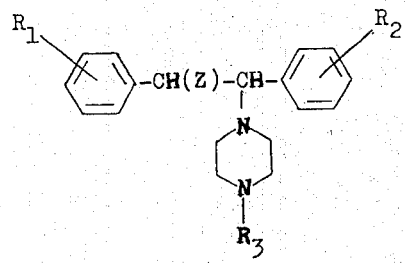

wherein $R_1$ and $R_2$ are each hydrogen, a halogen, nitro, hydroxy, an alkyl or methoxy; $R_3$ is a group of the formula:

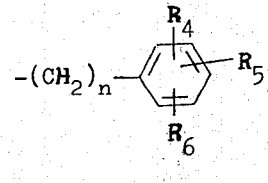

wherein $R_4$, $R_5$ and $R_6$ are each hydrogen, a halogen or methoxy and $n$ is an integer of 0 to 3, or a pyridyl; and Z is hydroxy or an acyloxy; with proviso that when $R_1$ and/or $R_2$ are hydroxy, Z is hydroxy, and their pharmaceutically acceptable salts, which have excellent analgesic and anti-tussive activities, and a process for the preparation thereof.

21 Claims, No Drawings

1,2-DIPHENYLETHANOLAMINE DERIVATIVES AND THEIR SALTS AND THE PREPARATION THEREOF

The present invention relates to novel, pharmaceutically active 1,2-diphenylethanolamine derivatives and their pharmaceutically acceptable salts and the preparation thereof. More particularly, it relates to 1,2-diphenylethanolamine derivatives of the following formula:

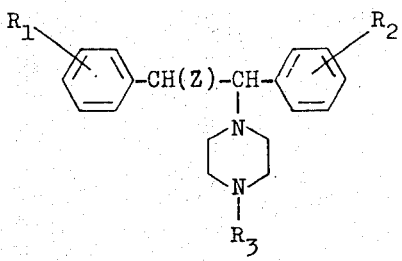

[I]

wherein $R_1$ and $R_2$ are each hydrogen, a halogen, nitro, hydroxy, an alkyl or methoxy; $R_3$ is a group of the formula:

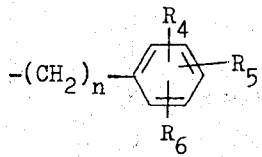

wherein $R_4$, $R_5$ and $R_6$ are each hydrogen, a halogen or methoxy and $n$ is an integer of 0 to 3, or a pyridyl; and Z is hydroxy or an acyloxy; with proviso that when $R_1$ and/or $R_2$ are hydroxy, Z is hydroxy, and their pharmaceutically acceptable salts, and further the preparation thereof.

In the present specification, "alkyl" denotes an alkyl having 1 to 5 carbon atoms, such as methyl, ethyl, propyl, isopropyl, butyl, isobutyl or pentyl, "acyloxy" denotes a lower alkanoyloxy (e.g. acetyloxy, propionyloxy, butyroyloxy or isobutyroyloxy), an aroyloxy (e.g. benzoyloxy or p-halobenzoyloxy) or an aralkanoyloxy (e.g. phenylacetyloxy) and "halogen" denotes fluorine, chlorine and bromine.

The compounds of the formula [I] have two adjacent asymmetric carbons in the molecule, and therefore, stereo and optical isomers exist. The present invention includes all of these isomers.

Some compounds having an analogous structure to that of the present compounds have been already described in French Pat. No. 1,313,095 and The Journal of Organic Chemistry, Vol. 14, page 771 (1949).

However, these compounds described in the literatures have little or impractical analgesic activity.

The novel ethanolamine derivatives of the formula [I] and their pharmaceutically acceptable salts exhibit superior pharmacological activities, such as analgesic and antitussive activities, and therefore, they are useful as a medicine.

An object of the present invention is to provide novel ethanolamine derivatives and their pharmaceutically acceptable salts having excellent pharmacological activities.

Another object of the invention is to provide a process for the preparation of the ethanolamine derivatives and their pharmaceutically acceptable salts.

A further object of the invention is to provide a pharmaceutical composition containing the compounds as set forth above as the active ingredient.

Still further object of the invention is to provide the use of the compound as set forth above as an analgesic.

These and other objects will be apparent from the description hereinafter.

The compounds of the present invention include those represented by the formula [I] as shown hereinbefore and their pharmaceutically acceptable acid addition salts. Among the present compounds, the preferred one is dl-erythro isomer and d-erythro isomer. Furthermore, the compounds of the formula [I], wherein $R_3$ is p-methoxybenzyl, are suitable.

Especially suitable compounds of this invention are as follows:

dl-Erythro-1-(p-chlorophenyl)-2-phenyl-2-[4-(p-methoxybenzyl)piperazin-1-yl]ethanol, dl-Erythro-1-phenyl-2-(o-chlorophenyl)-2-[4-(p-methoxybenzyl)piperazin-1-yl]ethanol, dl-Erythro-1-phenyl-2-(o-methoxyphenyl)-2-[4-(p-methoxybenzyl)piperazin-1-yl]ethanol, dl-Erythro-1-(p-tolyl)-2-(p-tolyl)-2-[4-(p-methoxybenzyl)piperazin-1-yl]ethanol, dl-Erythro-1-phenyl-2-(o-tolyl)-2-[4-(p-methoxybenzyl)piperazin-1-yl]ethanol, d-Erythro-1,2-diphenyl-2-[4-(p-methoxybenzyl)piperazin-1-yl]ethanol, and dl-Erythro-1-(m-tolyl)-2-phenyl-2-[4-(p-methoxybenzyl)piperazin-1-yl]ethanol, and their pharmaceutically acceptable acid addition salts.

The compounds of the formula [I] may be prepared by the following process.

That is, the compounds of the formula [I], wherein Z is hydroxy, may be prepared by reducing a 2-phenyl-2-piperazinylacetophenone derivative of the formula:

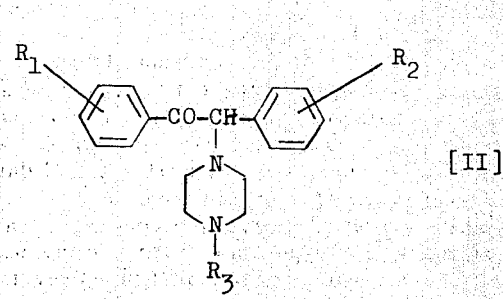

[II]

wherein $R_1$, $R_2$ and $R_3$ are as defined above. The compounds of the formula [I], wherein Z is an acyloxy, may be prepared by acylating the compound obtained above, wherein $R_1$ and/or $R_2$ are the group other than hydroxy, with an acylating agent.

The processes may be illustrated by the following reaction schemes:

dride in alcohols, or with lithium aluminum hydride in ether or dioxane, or by an electrolytic reduction. Moreover, it may also be carried out by using a mineral acid (e.g. hydrochloric acid or sulfuric acid) and a metal (e.g. iron or tin) in water or a dilute alcohol or by using sodium metal in an alcohol.

The acylation of the compound [III'] to the com-

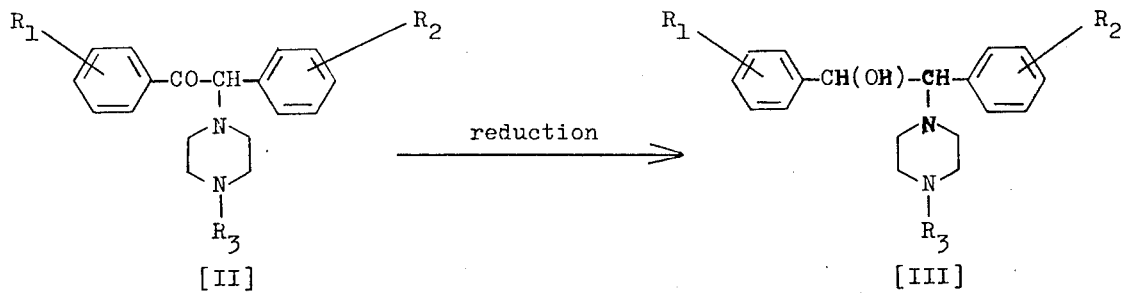

wherein $R_1$, $R_2$ and $R_3$ are as defined above, and pound [IV] may be carried out by conventional meth-

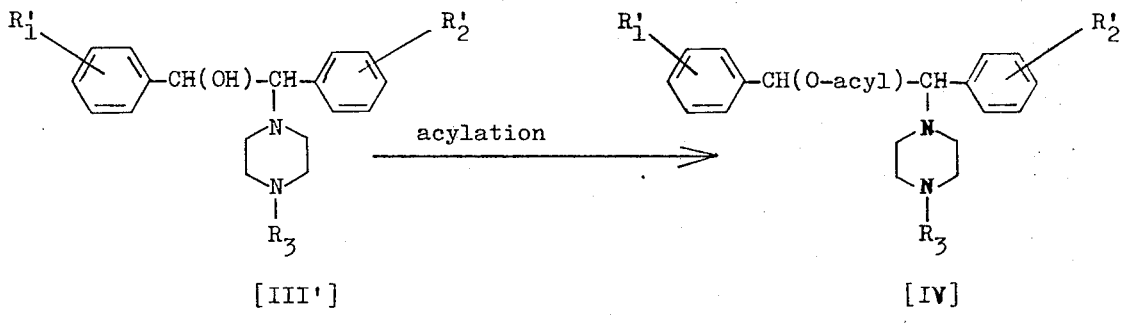

wherein $R_1'$ and $R_2'$ are each hydrogen, a halogen, nitro, an alkyl or methoxy.

The reduction of the compound [II] to the compound [III] may be carried out by conventional methods, for instance, by catalytically reducing the compound [II] in an inert solvent (e.g. methanol or ethanol) in the presence of a catalyst (e.g. palladium-carbon, platinum black or Raney nickel) or by reducing the compound [II] with a reducing agent, such as a metal hydride complex in a solvent, for instance, with sodium borohydride or sodium diethoxyaluminum hyods, and preferably, by reacting the compound [III'] with a carboxylic acid or its reactive derivative such as an acid halide or an acid anhydride in the presence or absence of a solvent. Suitable examples of the carboxylic acid are acetic acid, propionic acid, butyric acid, isobutyric acid, benzoic acid, p-halobenzoic acid, phenylacetic acid, or the like. As the solvent, there may be used any solvent which does not give any undesirable effect on the reaction, and for instance, an inert solvent, such as pyridine, benzene, toluene or xylene. Suitable reaction temperature may be 0 to 150° C, and the reaction may usually be carried out at a reflux temperature.

The starting material of the formula [II] may be prepared by reacting a 2-phenylacetophenone derivative of the formula:

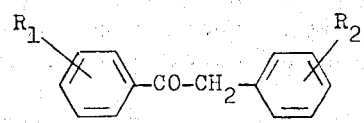

wherein $R_1$ and $R_2$ are as defined above, with a halogenating agent, such as bromine or N-bromosuccinimide, to give a 2-halogeno-2-phenylacetophenone derivative of the formula:

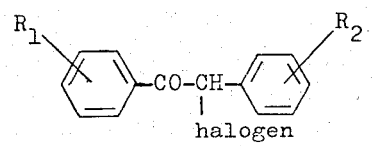

wherein $R_1$ and $R_2$ are as defined above, and reacting the resulting compound with a piperazine derivative of the formula:

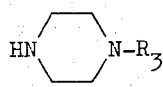

wherein $R_3$ is as defined above.

According to the above processes, the desired compound of the present invention may be obtained in a form of a free base or a salt depending on the kinds of the starting materials and the reaction conditions. When they are obtained in a form of a free base, they may be converted into their pharmaceutically acceptable salts of various inorganic or organic acid. Suitable acids include inorganic acids (e.g. hydrochloric acid, hydrobromic acid, hydroiodic acid, sulfuric acid or phosphoric acid) and organic acids (e.g. citric acid, maleic acid, fumaric acid tartaric acid, acetic acid, benzoic acid, lactic acid, methanesulfonic acid, 2-naphthalenesulfonic acid, salicylic acid or acetylsalicylic acid). When they are obtained in a form of a salt, they may be converted to a free base by a conventional method using a base.

The compounds of the present invention may be present in a form of dl-erythro, dl-threo, d-erythro, l-erythro, d-threo or l-threo. The mixture of these stereo and optical isomers may be isolated as follows. That is, the mixture is subjected to a recrystallization or various chromatographies, by which two optically inactive isomers, i.e. dl-erythro and dl-threo isomers, are isolated. The isomers are reacted with an optically active acid (e.g. d- or 1-2'-nitrotartranilic acid) to form the salts thereof, which are further subjected to a fractional crystallization and thereby they are resolved to the optically active isomers, i.e. d-isomer and l-isomer.

The activities of the present compounds are demonstrated by the following experimental tests.

1. Analgesic activity:

i. D'Amour-Smith method (cf. F. E. D'Amour and D. L. Smith, *J. Pharmacol.*, Vol. 72, page 74, 1941)

Thermal pain was induced by radiating heat light on the tail blacked with a black ink of male mice of ddN strain, weighing 9 to 12 g, using the modified apparatus of D'Amour-Smith. The analgesic $ED_{50}$-value was calculated from the number of positive animals showing the response time prolonged more than 100% compared with each before value.

ii. Phenylquinone method (cf. E. Siegmund, R. Cadmus and G. Lu, *Proc. Soc. Exptl. Biol. Med.*, Vol. 95, page 729, 1957)

Chemical pain was induced by an intraperitoneal injection of 0.1 ml/10 g body weight of 0.03% phenylquinone in 5% aqueous ethanol in female mice, weighing 18 to 22 g of ddN strain. Drugs were given 30 minutes before challenge of phenylquinone.

The test results are shown in the following Table 1.

Table 1

| Test Compound* | Analgesic $ED_{50}$ value (mg/kg) | |
|---|---|---|
| | D'Amour-Smith method (s.c.) | Phenylquinone method (p.o.) |
| A | — | 49.9 |
| B | 55.5 | 45.1 |
| C | 32.5 | 28.6 |
| D | 98.6 | 55.6 |
| E | 65.2 | 30.2 |
| F | 37.2 | 63.2 |
| Reference** compound | | |
| 1 | inactive | — |
| 2 | >320 | — |
| 3 | 233 | 53.3 |

[Note]:
*The test compounds are as follows:
A: dl-Erythro-1-(p-chlorophenyl)-2-phenyl-2-[4-(p-methoxy-benzyl)piperazin-1-yl]ethanol dihydrochloride
B: dl-Erythro-1-phenyl-2-(o-chlorophenyl)-2-[4-(p-methoxybenzyl)piperazin-1-yl]ethanol dihydrochloride
C: dl-Erythro-1-phenyl-2-(o-methoxyphenyl)-2-[4-(p-methoxybenzyl)piperazin-1-yl]ethanol dihydrochloride
D: dl-Erythro-1-(p-tolyl)-2-(p-tolyl)-2-[4-(p-methoxybenzyl)piperazin-1-yl]ethanol dihydrochloride
E: dl-Erythro-1-phenyl-2-(o-tolyl)-2-[4-(p-methoxybenzyl)piperzin-1-yl]ethanol dihydrochloride
F: d-Erythro-1,2-diphenyl-2-[4-(p-methoxybenzyl)piperazin-1-yl]ethanol dihydrochloride
**The reference compounds are as follows:
1: dl-Erythro-1,2-diphenyl-2-(4-methylpiperazin-1-yl)ethanol dihydrochloride (J. Org. Chem., Vol. 14, page 771, 1949)
2: dl-2-Phenyl-2-(4-benzylpiperazin-1-yl)acetophenone dihydrochloride (French Patent No. 1,313,095)
3: Aminopyrine (commercially available analgesic)

2. Anti-tussive activity (cf. K. Takagi, H. Fukuda and K. Yano, Yakugakuzasshi, Vol. 80, page 1497, 1960)

Male guinea-pigs, weighing 350 to 450 g, were used. Coughs were caused by successive mechanical stimulations with whiskers, and anti-tussive effects were evaluated by all or none of the cough. The Test Compounds F and G were intraperitoneally injected. As the results, the test compounds showed excellent anti-tussive activity in a dose of 5–40 mg/kg, and the activity of Test Compound F was more potent than that of codeine phosphate, and the activity of Test Compound G was comparable with that of codeine phosphate.

The Test Compound F used herein is as defined in Table 1, and Test Compound G is dl-erythro-1-(m-tolyl)-2-phenyl-2-[4-(p-methoxybenzyl)piperazine-1-yl]ethanol dihydrochloride.

The compounds [I] and their pharmaceutically acceptable salts of the present invention may be used as medicines, for example, in the form of pharmaceutical preparations containing the compound in admixture with an organic or inorganic, solid or liquid pharmaceutical adjuvants suitable for oral or parenteral adminstration. Pharmaceutically acceptable adjuvants are substances that do not react with the compounds, for example, water, gelatin, lactose, starch, cellulose, preferably microcrystalline cellulose, sodium carboxymethyl cellulose, calcium carboxymethyl cellulose, methyl cellulose, sorbitol, magnesium stearate, talc, vegetable oils, benzyl alcohol, gums, propylene glycol, polyalkylene glycols, methyl paraben and other known medicinal adjuvants. The pharmaceutical preparations may be, for example, powder, tablets, suppositories, or capsules, or in liquid form as solutions, suspensions, or emulsions. They may further contain other therapeutically valuable substances. The preparations are prepared by conventional methods.

A clinical dosage of the compound [I] or its pharmaceutically acceptable salt depends on body weight, age and administration routes, but it is generally in the range of 10 to 500 mg/day, preferably of 50 to 200 mg/day.

The preparation of the present compounds [I] and their pharmaceutically acceptable salts and further the compositions thereof are illustrated by the following Examples but not limited thereto. In the Examples, percentages are by weight unless otherwise specified.

EXAMPLE 1 dl-Erythro-1-phenyl-2-(o-chlorophenyl)-2-[4-(p-methoxybenzyl)piperazin-1-yl]ethanol dihydrochloride In methanol (400 ml) is dissolved 2-(o-chlorophenyl)-2-[4-(p-methoxybenzyl)piperazin-1-yl]acetophenone (97 g) and the mixture is made weakly alkaline with a 5 % aqueous solution of sodium hydroxide. To the mixture is added in portions sodium borohydride (1.1 g) under ice-cooling. After allowing to stand at room temperature overnight, the mixture is distilled under reduced pressure to removed methanol. To the resulting oily substance is added benzene (200 ml) and the mixture is washed with water three times. The benzene layer is dried over potassium carbonate and concentrated under reduced pressure. The resulting oily substance is dissolved in ethanol (50 ml) and thereto is added a 20 % ethanolic hydrochloric acid under ice-cooling. The precipitated crystals are separated by filtration and recrystallized from 80 % ethanol-water to give the titled compound (73 g), m.p. 215° – 216° C.

The free base of this compound (oily substance) is prepared by treating the dihydrochloride obtained above with a diluted aqueous solution of potassium carbonate by a conventional method.

Analysis for $C_{26}H_{29}N_2O_2Cl$: Calcd (%): C,71.47; H,6.69; N,6.41; Cl,8.11. Found (%): C,71.20; H,6.73; N,6.32; Cl,7.98. Mass spectrum m/e: $M^+$ 436.

The dimaleate of the compound is prepared by treating the free base obtained above with maleic acid in ethanol by a conventional method, m.p. 141° – 148° C (recrystallized from ethanol).

The difumarate of the compound has a melting point of 171° – 179° C (recrystallized from ethanol-ether).

Similarly, the dihydrobromide has a melting point of 246° – 248° C (recrystallized from aqueous ethanol).

EXAMPLE 2 dl-Erythro-1-(p-chlorophenyl)-2-phenyl-2-[4-(p-methoxybenzyl)piperazin-1-yl]ethanol dihydrochloride In methanol (300 ml) is dissolved 4'-chloro-2-phenyl-2-[4-(p-methoxybenzyl)piperazin-1-yl]acetophenone (55.5 g) and the mixture is made weakly alkaline with a 5 % aqueous solution of sodium hydroxide (3 ml). To the mixture is added in portions sodium borohydride (5.8 g) under ice-cooling. After allowing to stand at room temperature overnight, the mixture is distilled under reduced pressure to remove methanol. To the resulting oily substance is added benzene (200 ml) and the mixture is washed with water three times. The benzene layer is dried over potassium carbonate and concentrated under reduced pressure. The resulting oily substance is dissolved in ethanol (50 ml) and thereto is added a 20 % ethanolic hydrochloric acid under ice-cooling. The precipitated crystals are separated by filtration and recrystallized from methanol to give the titled compound (33 g), m.p. 207° – 211° C.

EXAMPLE 3 dl-Erythro-1-(p-tolyl)-2-(p-tolyl)-2-[4-(p-methoxybenzyl)piperazin-1-yl]ethanol dihydrochloride In methanol (100 ml) is dissolved 4'-methyl-2-(p-tolyl)-2-[4-(p-methoxybenzyl)piperazin-1-yl]acetophenone (20 g) and the mixture is made weakly alkaline with a 5 % aqueous solution of sodium hydroxide (2 ml). To the mixture is added in portions sodium borohydride (2.5 g) under ice-cooling. After allowing to stand at room temperature overnight, the mixture is distilled under reduced pressure to removed methanol. To the resulting oily substance is added benzene (100 ml) and the mixture is washed with water three times. The benzene layer is dried over potassium carbonate and concentrated under reduced pressure. The resulting oily substance is dissolved in ethanol (30 ml) and thereto is added a 20 % ethanolic hydrochloric acid under ice-cooling. The precipitated crystals are separated by filtration and recrystallized from 80 % ethanol-water to give the titled compound (11 g), m.p. 228° – 234° C.

EXAMPLE 4 dl-Erythro-1-phenyl-2-(o-methoxyphenyl)-2-[4-(p-methoxybenzyl)piperazin-1-yl]ethanol dihydrochloride In methanol (30 ml) is dissolved 2-(o-methoxyphenyl)-2-[4-(p-methoxybenzyl)piperazin-1-yl]acetophenone (4.6 g) and the mixture is made weekly alkaline with a 5 % aqueous solution of sodium hydroxide (1 ml). To the mixture is added in portions sodium borohydride (0.55 g) under ice-cooling. After allowing to stand at room temperature overnight, the mixture is distilled under reduced pressure to remove methanol. The resulting oily substance is dissolved in benzene (50 ml) and the mixture is washed with water three times. The benzene layer is dried over potassium carbonate and concentrated under reduced pressure. The resulting oily substance is dissolved in ethanol (20 ml) and thereto is added a 20 % ethanolic hydrochloric acid under ice-cooling. The precipitated crystals are separated by filtration and recrystallized from a 80 % ethanol-water to give the titled compound (2.3 g), m.p. 211° – 219° C.

EXAMPLE 5 dl-Erythro-1,2-diphenyl-2-[4-(p-methoxybenzyl)piperazin-1-yl]ethanol and
dl-threo-1,2-diphenyl-2-[4-(p-methoxybenzyl)-piperazin-1-yl]ethanol In methanol (300 ml) is dissolved 2-phenyl-2-[4-p-methoxybenzyl)piperazin-1-yl]acetophenone dihydrochloride (28 g) and the mixture is made weakly alkaline with a 5 % aqueous solution of sodium hydroxide. To the mixture is added sodium borohydride (4.8 g). After stirring the mixture at room temperature overnight, the precipitated crystals are separated by filtration and recrystallized from methanol to give the titled dl-erythroisomer (12 g), m.p. 117° – 119° C.

The mother liquor obtained after the above separation of the crystals is combined with that obtained after the above recrystallization and the mixture is concentrated under reduced pressure to give an oily substance (8.5 g). The oily substance is subjected to a silica gel column chromatography and eluted with a 3 % methanol-chloroform. From the first half eluate dl-threo isomer is obtained, and from the second half elute dl-erythro isomer is obtained. These isomers are recrystallized from methanol to give dl-threo isomer (2 g), m.p. 132° – 134° C and dl-erythro isomer (3 g), m.p. 117° – 119° C.

EXAMPLE 6

Various compounds of the formula:

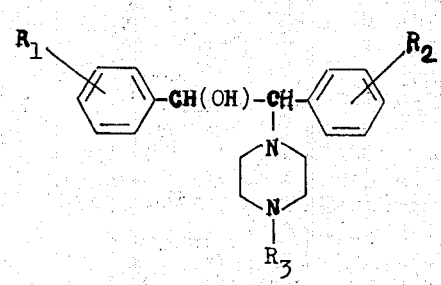

as listed in the following Table 2 are prepared in the same manner as described in Example 5.

Table 2

| $R_1$ | $R_2$ | $R_3$ | Isomer (dl-) | Melting point (° C) |
|---|---|---|---|---|
| H | H | 4-Cl-phenyl | Erythro | 173 – 175 |
| H | H | 4-Cl-phenyl | Threo | 188 – 190 |
| H | H | 2-Cl-phenyl | Erythro | 165 – 167 |
| H | H | 2-Cl-phenyl | Threo | 150 – 152 |
| H | H | -CH$_2$-(4-Cl-phenyl) | Erythro | 138 – 140 |
| H | H | -CH$_2$-(4-Cl-phenyl) | Threo | 150 – 151 |

Table 2-continued

| R₁ | R₂ | R₃ | Isomer (dl-) | Melting point (° C) |
|---|---|---|---|---|
| H | H | —CH₂—C₆H₅ | Erythro | 230 – 235* |
| H | H | —CH₂—C₆H₅ | Threo | 220* |
| H | H | —CH₂—C₆H₂(OCH₃)₃ | Threo | 171 – 174 |
| p-OCH₃ | H | —CH₂—C₆H₄—OCH₃ | Threo | 203 – 206* |
| p-Cl | H | —CH₂—C₆H₄—OCH₃ | Threo | 127 – 128 |
| H | p-Cl | —CH₂—C₆H₄—OCH₃ | Erythro | 205 – 209* |
| H | p-OCH₃ | —CH₂—C₆H₄—OCH₃ | Erythro | 202 – 207* |
| p-OH | H | —CH₂—C₆H₄—OCH₃ | Erythro | 185 – 188* |
| H | p-NO₂ | —CH₂—C₆H₄—OCH₃ | Erythro | 192 – 196* |
| o-OCH₃ | H | —CH₂—C₆H₄—OCH₃ | Erythro | 206 – 210* |
| o-CH₃ | H | —CH₂—C₆H₄—OCH₃ | Erythro | 211 – 217* |
| p-CH₃ | p-Cl | —CH₂—C₆H₄—OCH₃ | Erythro | 209 – 212* |
| p-CH₃ | o-Cl | —CH₂—C₆H₄—OCH₃ | Erythro | 138 – 141* |
| p-CH₃ | o-OCH₃ | —CH₂—C₆H₄—OCH₃ | Erythro | 223 – 228* |
| H | H | 2-pyridyl | Erythro | 166 – 169 |
| H | H | 2-pyridyl | Threo | 135 – 138 |

Table 2-continued

| $R_1$ | $R_2$ | $R_3$ | Isomer (dl-) | Melting point (°C) |
|---|---|---|---|---|
| H | H | -CH$_2$CH$_2$-C$_6$H$_5$ | Erythro | 134 – 137 |
| H | H | -CH$_2$-C$_6$H$_2$(OCH$_3$)$_3$ | Erythro | 225 – 228* |
| H | m-OCH$_3$ | -CH$_2$-C$_6$H$_4$-OCH$_3$ | Erythro | >240* |
| H | m-CH$_3$ | -CH$_2$-C$_6$H$_4$-OCH$_3$ | Erythro | 224 – 228* |
| H | p-NO$_2$ | -CH$_2$-C$_6$H$_4$-OCH$_3$ | Threo | 218 – 223* |
| H | o-CH$_3$ | -CH$_2$-C$_6$H$_4$-OCH$_3$ | Threo | 219 – 223* |
| p-Cl | H | -CH$_2$-C$_6$H$_4$-OCH$_3$ (o-OCH$_3$) | Erythro | 214 – 217* |
| H | o-CH$_3$ | -CH$_2$-C$_6$H$_4$-OCH$_3$ (o-OCH$_3$) | Erythro | 221 – 225* |
| H | o-CH$_3$ | -CH$_2$-C$_6$H$_4$-OCH$_3$ (m-OCH$_3$) | Erythro | 220 – 223* |
| H | o-Cl | -CH$_2$-C$_6$H$_4$-OCH$_3$ (m-OCH$_3$) | Erythro | >240* |
| H | o-Cl | -CH$_2$-C$_6$H$_4$-OCH$_3$ (o-OCH$_3$) | Erythro | 225 – 228* |
| m-Cl | H | -CH$_2$-C$_6$H$_4$-OCH$_3$ | Erythro | 216 – 221* |
| H | m-Cl | -CH$_2$-C$_6$H$_4$-OCH$_3$ | Erythro | 215 – 220* |

Note]: *Dihydrochloride

EXAMPLE 7 dl-Erythro-1-phenyl-2-(o-tolyl)-2-[4-(p-methoxybenzyl)-piperazin-1-yl]ethanol dihydrochloride In ethanol (20 ml) is dissolved 2-(o-tolyl)-2-[4-(p-methoxybenzyl)piperazin-1-yl]acetophenone (2 g) and the mixture is catalytically reduced with platinum oxide (50 mg) under hydrogen gas at 50° – 60° C. When the theoretical amount of hydrogen is absorbed, the reaction is stopped. The reaction mixture is filtered and the filtrate is concentrated under reduced pressure to give a colorless oily substance (2 g). The oily substance is dissolved in ethanol and thereto is added a 20 % ethanolic hydrochloric acid. After cooling, the precipitated crystals are separated by filtration and recrystallized from 90 % ethanol-water to give the titled compound (1.2 g), m.p. 211° – 217° C.

EXAMPLE 8

Various compounds of the formula:

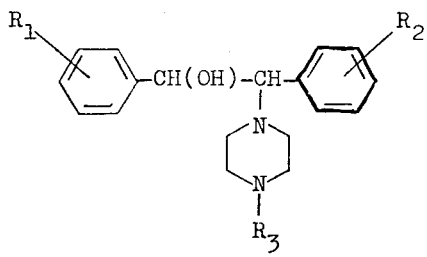

as listed in the following Table 3 are prepared in the same manner as described in Example 7.

EXAMPLE 9 dl-Erythro-1,2-diphenyl-1-propionyloxy-2-[4-(p-methoxybenzyl)piperazin-1-yl]ethane dihydrochloride In anhydrous pyridine (5 ml) is dissolved dl-erythro-1,2-diphenyl-2-[4-(p-methoxybenzyl)piperazin-1-yl]ethanol (1 g) obtained in the above Example 5 and thereto is added propionic acid anhydride (5 ml). After allowing to stand at room temperature overnight, the mixture is poured onto ice-water and the separated oily substance is extracted with benzene. The benzene layer is washed with a 5 % aqueous solution of sodium carbonate and then with water, dried over anhydrous potassium carbonate and distilled under reduced pressure to remove benzene. The resulting oily substance is dissolved in ethanol and thereto is added a 20 % ethanolic hydrochloric acid to give the crystals of the titled compound (0.7 g), m.p. 161° – 165° C.

EXAMPLE 10 dl-Erythro-1,2-diphenyl-1-isobutyryloxy-2-[4-(p-methoxybenzyl)piperazin-1-yl]ethane dihydrochloride In anhydrous pyridine (5 ml) is dissolved dl-erythro-1,2-diphenyl-2-[4-(p-methoxybenzyl)piperazin-1-yl]ethanol (2 g) and thereto is added isobutyric acid anhydride (5 ml). After stirring at room temperature overnight, the mixture is poured onto ice-water and the separated oily substance is extracted with benzene. The benzene layer is washed with a 5 % aqueous solution of sodium carbonate and then with water, dried over anhydrous potassium carbonate and distilled to remove benzene. The resulting oily substance is dissolved in ethanol and thereto is added a 20 % ethanolic hydrochloric acid to give the crystals of the titled compound (2.3 g), m.p. 144° – 146° C.

Table 3

| $R_1$ | $R_2$ | $R_3$ | Isomer (dl-) | Melting point (° C) |
|---|---|---|---|---|
| H | H | ⟨phenyl⟩ | Erythro | 100 – 103 |
| H | H | H₃CO–⟨phenyl⟩ | Threo | 160 – 162 |
| H | H | H₃CO–⟨phenyl⟩ | Erythro | 163 – 165 |
| p-CH₃ | H | –CH₂–⟨phenyl⟩–OCH₃ | Erythro | 240 (dec.)* |
| m-CH₃ | H | –CH₂–⟨phenyl⟩–OCH₃ | Erythro | 211 – 219* |
| H | p-CH₃ | –CH₂–⟨phenyl⟩–OCH₃ | Erythro | 224 – 232* |

[Note]: *Dihydrochloride

EXAMPLE 11

Various compounds of the formula:

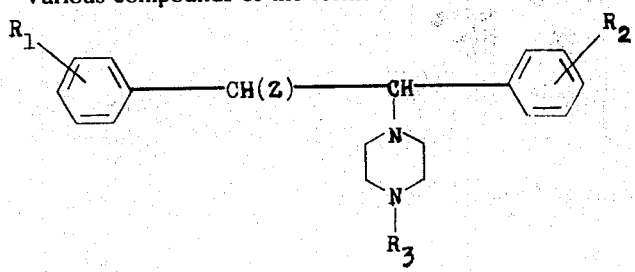

as listed in the following Table 4 are prepared in the same manner as described in Example 10.

Table 4

| $R_1$ | $R_2$ | $R_3$ | Z | Isomer (dl-) | Melting point (°C) |
|---|---|---|---|---|---|
| H | H | —CH₂—(phenyl) | —OCOCH₃ | Erythro | 148 – 153* |
| H | H | —CH₂—(3,4,5-tri-OCH₃ phenyl) | —OCOC₂H₅ | Erythro | 167 – 170 |
| H | H | —(2-pyridyl) | —OCOCH₃ | Erythro | 185 – 191* |
| p-CH₃ | H | —CH₂—(p-OCH₃ phenyl) | —OCOC₂H₅ | Erythro | 138 – 141* |
| H | H | —CH₂—(p-OCH₃ phenyl) | —OCOCH₃ | Erythro | 148 – 153* |
| H | H | —CH₂—(phenyl) | —OCOC₂H₅ | Erythro | 153 – 158* |
| H | H | —CH₂—(3,4,5-tri-OCH₃ phenyl) | —OCOCH₃ | Erythro | 180 – 185* |
| H | H | —CH₂—(3,4,5-tri-OCH₃ phenyl) | —OCOC₂H₅ | Erythro | 167 – 170* |
| p-CH₃ | o-Cl | —CH₂—(p-OCH₃ phenyl) | —OCOC₂H₅ | Erythro | 138 – 141* |
| H | o-Cl | —CH₂—(p-OCH₃ phenyl) | —OCOCH(CH₃)₂ | Erythro | 173 – 183* |
| H | o-OCH₃ | —CH₂—(p-OCH₃ phenyl) | —OCOC₂H₅ | Erythro | 213 – 217* |
| p-Cl | H | —CH₂—(p-OCH₃ phenyl) | —OCOC₂H₅ | Erythro | 150 – 154* |

Table 4-continued

| R₁ | R₂ | R₃ | Z | Isomer (dl-) | Melting point (° C) |
|---|---|---|---|---|---|
| H | o-Cl |  | —OCOC₂H₅ | Erythro | 168 – 172* |

[Note]: *Dihydrochloride

EXAMPLE 12 d-Erythro-1,2-diphenyl-2-[4-(p-methoxybenzyl)piperazin-1-yl]ethanol dihydrochloride and 1-erythro-1,2-diphenyl-2-[4-(p-methoxybenzyl)piperazin-1-yl]ethanol dihydrochloride In hot ethanol (50 ml) are dissolved dl-erythro-1,2-diphenyl-2-[4-(p-methoxybenzyl)piperazin-1yl]ethanol (10 g) and d-2'-nitrotartranilic acid (13.4 g) and the mixture is cooled. The precipitated crystals (16.5 g) are repeatedly (four times) recrystallized from 85 % ethanol-water to give 1-erythro-1,2-diphenyl-2-[4-(p-methoxybenzyl)piperazin-1-yl]ethanol di-d-2'-nitrotartranilate (4.7 g), m.p. 186.5° – 188° C, $[\alpha]_D^{25} = +37°$ (C=1, methanol).

The di-d-2'-nitrotartranilate (4.7 g) thus obtained is dissolved in water (30 ml) and made weakly alkaline with a 5 % aqueous solution of sodium hydroxide and the separated oily substance is extracted with chloroform. The chloroform layer is washed with water, dried over anhydrous potassium carbonate and distilled to remove chloroform. The resulting oily substance is dissolved in ethanol (10 ml) and thereto is added a 20 % ethanolic hydrochloric acid under ice-cooling. The precipitated crystals are separated by filtration and recrystallized twice from 80 % ethanol-water to give the desired 1-erythro-1,2-diphenyl-2-[4-(p-methoxybenzyl)piperazin-1-yl]-ethanol dihydrochloride (1.8 g), m.p. 223.5° – 225° C, $[\alpha]_D^{25} = -32.7°$ (C=0.75, water).

Similarly, d-erythro-1,2-diphenyl-2-[4-(p-methoxybenzyl)piperazin-1-yl]ethanol dihydrochloride [0.6 g, m.p. 223° – 226° C, $[\alpha]_D^{25} = +32°$ (C=1, water)] is prepared from dl-erythro-1,2-diphenyl-2-[4-(p-methoxybenzyl)piperazin-1-yl]ethanol (3 g) and 1-2'-nitrotartranilic acid (4 g).

The starting 2-phenyl-2-[4-(p-methoxybenzyl)piperazin-1-yl]acetophenone dihydrochloride used in the above Example is prepared as follows:

In chloroform (200 ml) is dissolved 2-phenylacetophenone (25.5 g) and thereto is added a solution of bromine (22 g) in chloroform (100 ml) and the mixture is stirred at room temperature for 5 hours and then allowed to stand overnight. After distilling off chloroform, to the resulting residue is added methanol. The precipitates are filtered off and the filtrate is subjected to a silica gel chromatography and eluted with chloroform. The eluates are collected and distilled to remove chloroform to give 2-bromo-2-phenylacetophenone (26 g) as an oily substance.

In ethanol (200 ml) are dissolved the 2-bromo-2-phenylacetophenone (11.0 g) thus obtained and p-methoxybenzylpiperazine (8.2 g) and thereto is added triethylamine (7 ml), and the mixture is refluxed for 4 hours. After distilling off ethanol, the resulting oily substance is extracted with chloroform. The chloroform layer is separated, washed with an aqueous solution of sodium hydroxide, dried and distilled to remove chloroform. The resulting residue is dissolved in acetone and thereto is added etheric hydrochloric acid. The precipitated crystals are separated by filtration and recrystallized from ethanol to give the desired compound (16.5 g), m.p. 180° – 183° C.

Example 13

| | |
|---|---|
| dl-Erythro-1-phenyl-2-(o-chlorophenyl)-2-[4-(p-methoxybenzyl)piperazin-1-yl]-ethanol dihydrochloride | 50 g |
| Starch | 110 g |
| Calcium carboxymethyl cellulose | 30 g |
| Hydroxypropyl cellulose | 9 g |
| Magnesium stearate | 1 g |

The above components are blended, granulated and made into tablets in accordance with the conventional method. The 1,000 tablets each weighing 200 mg are formed.

Example 14

| | |
|---|---|
| dl-Erythro-1-phenyl-2-(o-chlorophenyl)-2-[4-(p-methoxybenzyl)piperazin-1-yl]-ethanol dihydrochloride | 25 g |
| Starch | 20 g |
| Lactose | 50 g |
| Talc | 5 g |

The above components are blended, granulated and filled into 1,000 capsules in accordance with the conventional method.

What is claimed is:
1. A 1,2-diphenylethanolamine derivative of the formula:

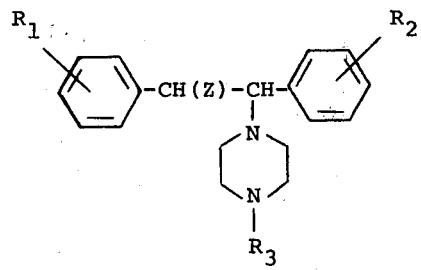

wherein R₁ and R₂ are each hydrogen, chlorine, nitro, hydroxy, methyl or methoxy; R₃ is a group of the formula:

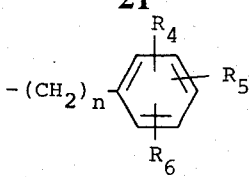

wherein $R_4$, $R_5$ and $R_6$ are each hydrogen, chlorine or methoxy and $n$ is an integer of 0, 1 or 2, or pyridyl; and Z is hydroxy or an alkanoyloxy selected from the group consisting of acetyloxy, propionyloxy, butyryloxy or isobutryloxy; with the proviso that when $R_1$ and/or $R_2$ are hydroxy, Z is hydroxy, or a pharmaceutically acceptable acid addition salt thereof.

2. A 1,2-diphenylethanolamine derivative of the formula:

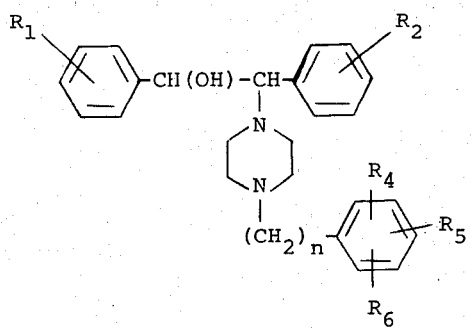

wherein $R_1$ and $R_2$ are each hydrogen, a chlorine, nitro, hydroxy, methyl or methoxy; $R_4$, $R_5$ and $R_6$ are each hydrogen, chlorine or methoxy; and $n$ is an integer of 0, 1 or 2, or a pharmaceutically acceptable acid addition salt thereof.

3. A 1,2-diphenylethanolamine derivative of the formula:

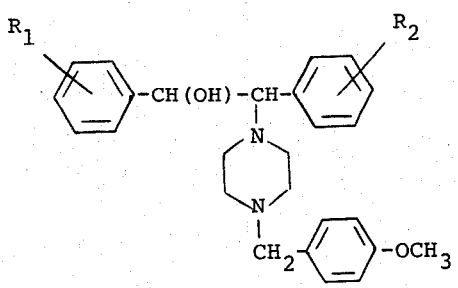

wherein $R_1$ and $R_2$ are each hydrogen, chlorine, nitro, hydroxy, methyl or methoxy, or a pharmaceutically acceptable acid addition salt thereof.

4. 1-Phenyl-2-(o-chlorophenyl)-2-[4-(p-methoxybenzyl)-piperazin-1-yl]ethanol or a pharmaceutically acceptable acid addition salt thereof.

5. 1-(p-Chlorophenyl)-2-phenyl-2-[4-(p-methoxybenzyl)-piperazin-1-yl]ethanol or a pharmaceutically acceptable acid addition salt thereof.

6. 1-(p-Tolyl)-2-(p-tolyl)-2-[4-(p-methoxybenzyl)-piperazin-1-yl]ethanol or a pharmaceutically acceptable acid addition salt thereof.

7. 1-Phenyl-2-(o-tolyl)-2-[4-(p-methoxybenzyl)-piperazin-1-yl]ethanol or a pharmaceutically acceptable acid addition salt thereof.

8. 1-Phenyl-2-(o-methoxyphenyl)-2-[4-(p-methoxybenzyl)piperazin-1-yl]ethanol or a pharmaceutically acceptable acid addition salt thereof.

9. 1-(m-Tolyl)-2-phenyl-2-[4-(p-methoxybenzyl)-piperazin-1-yl]ethanol or a pharmaceutically acceptable acid addition salt thereof.

10. 1,2-Diphenyl-2-[4-(p-methoxybenzyl)piperazin-1-yl]ethanol or a pharmaceutically acceptable acid addition salt thereof.

11. A compound as set forth in claim 1 which is an erythro isomer.

12. A compound as set forth in claim 1 which is a dl-erythro isomer.

13. A compound as set forth in claim 1 which is a d-erythro isomer.

14. The compound as set forth in claim 5 which is a dl-erythro isomer.

15. The compound as set forth in claim 4 which is a dl-erythro isomer.

16. The compound as set forth in claim 10 which is a d-erythro isomer.

17. A pharmaceutical composition consisting essentially of a compound as set forth in claim 1 as the active ingredient.

18. A pharmaceutical composition consisting essentially of the compound as set forth in claim 14 as the active ingredient.

19. A pharmaceutical composition consisting essentially of the compound as set forth in claim 15 as the active ingredient.

20. A pharmaceutical composition of claim 17 as an analgesic.

21. The compound as set forth in claim 7 which is a dl-erythro isomer.

* * * * *